United States Patent [19]
Bailey et al.

[11] Patent Number: 5,605,457
[45] Date of Patent: Feb. 25, 1997

[54] IMPLANT CONNECTOR

[75] Inventors: A. Gregory Bailey, Alabaster; Aubrey C. Folsom, Jr., Pelham, both of Ala.

[73] Assignee: Crystal Medical Technology, a division of Folsom Metal Products, Inc., Birmingham, Ala.

[21] Appl. No.: 387,320

[22] Filed: Feb. 13, 1995

[51] Int. Cl.$^6$ .................................................. A61K 8/00
[52] U.S. Cl. .......................... 433/174; 433/173; 606/73
[58] Field of Search ................................. 433/169, 172, 433/173, 174, 175; 606/65, 73; 411/309, 307, 310, 311, 411, 414, 415, 423, 426; 285/333, 334

[56] References Cited

U.S. PATENT DOCUMENTS

| | | |
|---|---|---|
| 3,579,831 | 5/1971 | Stevens et al. . |
| 3,672,058 | 6/1972 | Nikoghossian . |
| 3,799,229 | 3/1974 | Johnson ................................. 411/307 |
| 3,863,344 | 2/1975 | Pillet . |
| 3,955,280 | 5/1976 | Sheer . |
| 3,981,079 | 9/1976 | Lenczyaki . |
| 4,016,651 | 4/1977 | Kawahara et al. . |
| 4,229,169 | 10/1980 | Smith et al. ............................. 433/174 |
| 4,318,696 | 3/1982 | Kasama et al. ......................... 433/173 |
| 4,324,550 | 4/1982 | Reuther et al. ......................... 433/174 |
| 4,359,318 | 11/1982 | Gittleman ............................... 433/173 |
| 4,406,623 | 9/1983 | Grafelmann et al. .................... 433/174 |
| 4,568,285 | 2/1986 | Chiaramonte et al. ................. 433/173 |
| 4,615,338 | 10/1986 | Ilizarov et al. . |
| 4,631,031 | 12/1986 | Richter ................................... 433/173 |
| 4,653,486 | 3/1987 | Coker . |
| 4,671,768 | 6/1987 | Ton .......................................... 433/174 |
| 4,684,555 | 8/1987 | Neumeyer ................................ 428/36 |
| 4,707,001 | 11/1987 | Johnson ............................... 285/332.3 |
| 4,713,004 | 12/1987 | Linkow et al. ........................ 433/174 |
| 4,826,434 | 5/1989 | Krueger ................................. 433/174 |
| 4,842,464 | 6/1989 | Green ..................................... 411/307 |
| 4,881,897 | 11/1989 | Franek et al. ........................... 433/169 |
| 4,938,694 | 7/1990 | Ledermann ............................. 433/173 |
| 5,000,686 | 3/1991 | Lazzara et al. ......................... 433/174 |
| 5,007,835 | 4/1991 | Valen ...................................... 433/174 |
| 5,022,860 | 6/1991 | Lazzara et al. ......................... 433/173 |
| 5,026,280 | 6/1991 | Dürr et al. ............................. 433/175 |
| 5,040,982 | 8/1991 | Stefan-Dogar ......................... 433/169 |
| 5,061,181 | 10/1991 | Niznick ................................... 433/174 |
| 5,078,607 | 1/1992 | Niznick ................................... 433/174 |
| 5,092,635 | 3/1992 | DeLange et al. ....................... 285/334 |
| 5,114,343 | 5/1992 | Musikanti et al. ..................... 433/173 |
| 5,133,662 | 7/1992 | Metcalfe ................................. 433/169 |
| 5,174,755 | 12/1992 | Fukuda ................................... 433/173 |
| 5,195,892 | 3/1993 | Gersberg ................................ 433/174 |
| 5,199,873 | 4/1993 | Schulte et al. ......................... 433/174 |
| 5,234,430 | 8/1993 | Huebner ................................... 606/60 |
| 5,238,405 | 8/1993 | Marlin .................................... 433/173 |
| 5,246,369 | 9/1993 | Paulmaire .............................. 433/173 |
| 5,259,398 | 11/1993 | Vrespa ................................... 128/898 |
| 5,269,686 | 12/1993 | James .................................... 433/174 |

*Primary Examiner*—Cary E. O'Connor
*Attorney, Agent, or Firm*—Veal & Associates

[57] ABSTRACT

A threaded connection for use in medical implant surgery which utilizes a thread profile which includes a load flank, a stab flank, a root intermediate the stab flank and load flank, and a crest intermediate the load flank and stab flank. The distance, measured paraxially, which the screw moves one complete revolution of the connection, is the lead of the thread. In the invention, the lead varies for either the male or female member of the connector such that the load flank, effectively, is moved away from axial interference with the cooperative member as the thread is "made up" or engaged. Accordingly, the load flank interface along the length of the connection is stressed, rather than having the load flank interface stressed predominately at the end turns of the thread, as often occurs under loading of the thread. In this manner, the stress loading of the thread is spread over the multiple turns of the thread, and pre-load is not lost by the yielding of the end turn.

16 Claims, 6 Drawing Sheets

FIG 6A
PRIOR ART
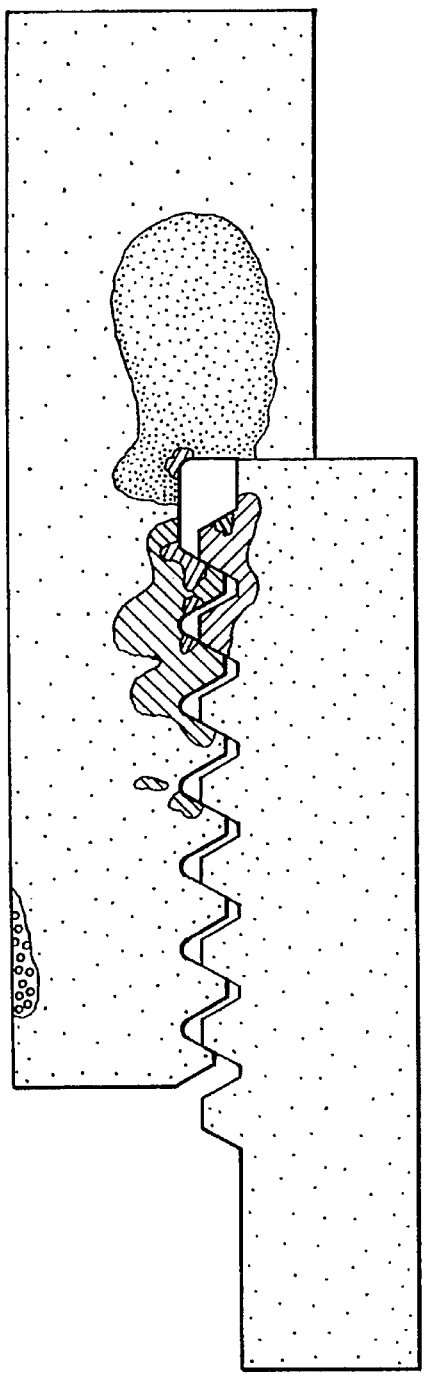
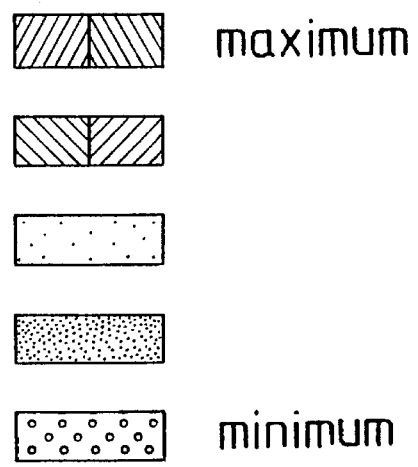
maximum
minimum

FIG. 6B
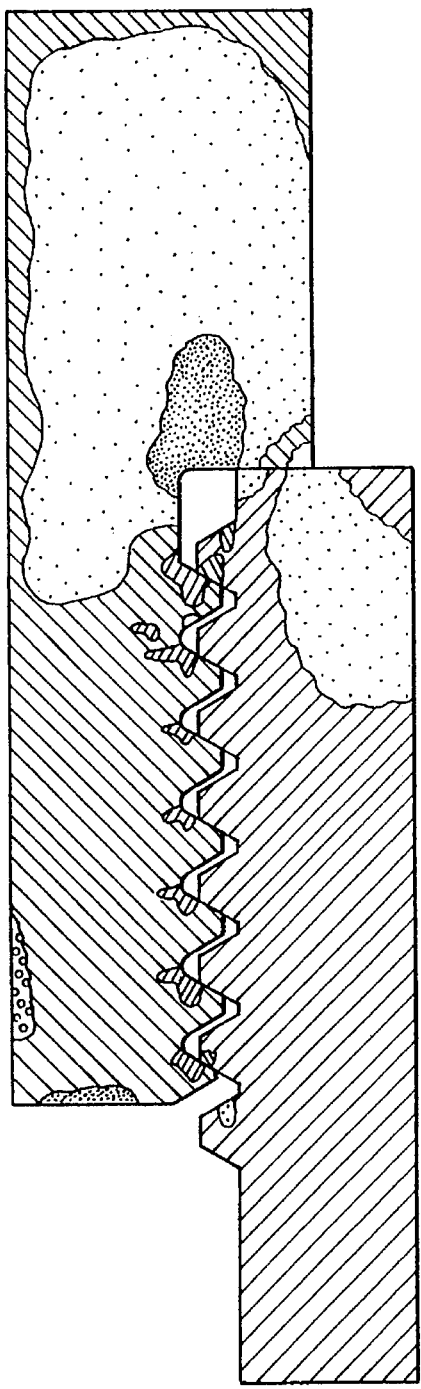
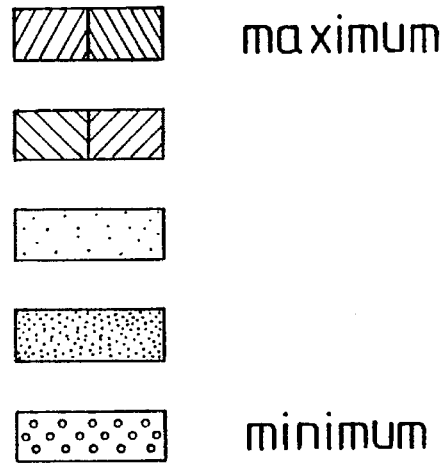

IMPLANT CONNECTOR

FIELD OF THE INVENTION

The present invention relates to prosthetic implantation of devices which are osseointegrated into bone. In more particularity, the present invention relates to the field of connectors used in such implants that secure the prosthesis to the implanted portion of the device. The present invention relates to the design of the thread profile so as to maximize the effectiveness of the connection within the implant/prosthesis assembly.

BACKGROUND

The prior art of implants extends back, at least, into the last century; however, only in the last twenty-five years have implants such as hip replacements, knee replacements and dental implants been widely used. These devices often employ threaded connections to fasten components of the prosthetic assembly together. Reported common problems noted by practitioners are breakage of the screw and loosening of the screw fixating the prosthesis in U.S. Pat. No. 5,213,500, for example. It is believed that one cause of the failure of the threaded connection is the stress imposed on selected threads along the connection. On conventional straight V-threads, this thread is the last engaged thread closest in proximity to the head of the screw or bolt. A nominally manufactured component can place portions of the threads in stress conditions above the yield strength of the material, resulting in permanent deformation of the thread. This yielding may lead to a loss of preload tension in the connection, leading to relative motion between the joined components, and compromising the function of the prosthesis. Likewise, dynamic fatigue of the overloaded fastener can lead to catastrophic failure. These stress concentrations are compounded by the physical size restraints placed on prosthetic components. The materials which are available to the designer to choose from, to wit, -polymers, metals, and composites- oftentimes exhibit creep characteristics. The stress-raising factors encountered in implants aggravate the tendency of these materials to have time-dependent strain at stress levels below yield.

SUMMARY OF THE INVENTION

It is the object of the present invention to distribute the loading of the threads of the prosthetic connectors over a greater number of threads such that stress levels are minimized.

Another object of the invention is to reduce the necessity of removing and reworking the implant connectors due to failure of the thread elements.

These and other objects and advantages of the present invention are accomplished by a combination of features of thread design which create a thread profile unlike any known profile used in the implant art. Specifically, the present invention utilizes a variation in the lead of the thread to more evenly distribute the stresses caused by torque and preload forces. The distance, measured paraxially, which the screw moves during one complete revolution of the connector is the lead of the thread. Specifically, the present invention is directed toward the thread interaction, regardless of the thread type, and is applicable with truncated threads or other conventional thread types. Regardless of the thread type, there will be a surface formed on the thread which serves as the load flank and a surface which serves as the stab flank. Intermediate these surfaces, the turns of the thread along the connector form a root and crest. In the invention, the lead of the thread along the length of the connector changes for either the male or female member of the connector such that the load flank, effectively, is moved to reduce the axial interference as the thread is "made up" or engaged. Accordingly, the load flank interface along the length of the connection is stressed, rather than having the load flank interface stressed predominately at the end turns of the thread, as often occurs under tension preloading or loading of the thread. In this manner, the tensional loading of the thread is distributed over the multiple turns of the thread, and pre-load is not lost by the yielding of a particular turn.

In the invention, the lead of the thread of one of the two coupled members is varied such that the movement of the load flank on that member per revolution, which may be conceptually considered the incremental lead per turn, and the separation of successive load flanks along the connector change along the threads, such that the load flank of the thread having the nominal lead is less distant from the next closest load flank than the next closest load flank is from the next load flank spaced toward the shoulder. Accordingly, the separation between identical points on the thread such as load flanks may be given by the formula:

$$L=k+n(x)$$

Where L is the incremental lead, k is a nominal or reference lead, n is the incremental deviation from nominal thread lead, and x is the number of increments over which the error applies. Thus, the lead will vary along the length of the connector. Further, x may be positive or negative depending on the location of the reference leads. It may also be seen that the lead may be varied to increase or decrease.

BRIEF DESCRIPTION OF THE DRAWINGS

Apparatus embodying features of our invention are depicted in the accompanying drawings which form a portion of this disclosure and wherein:

FIG. 6a is a prior art representation of the stress placed on the connector as determined by finite elemental analysis.

FIG. 6b is a representation of the stress placed on the connector of the present invention as determined by finite elemental analysis.

DESCRIPTION OF THE PREFERRED EMBODIMENT

Figure 1:
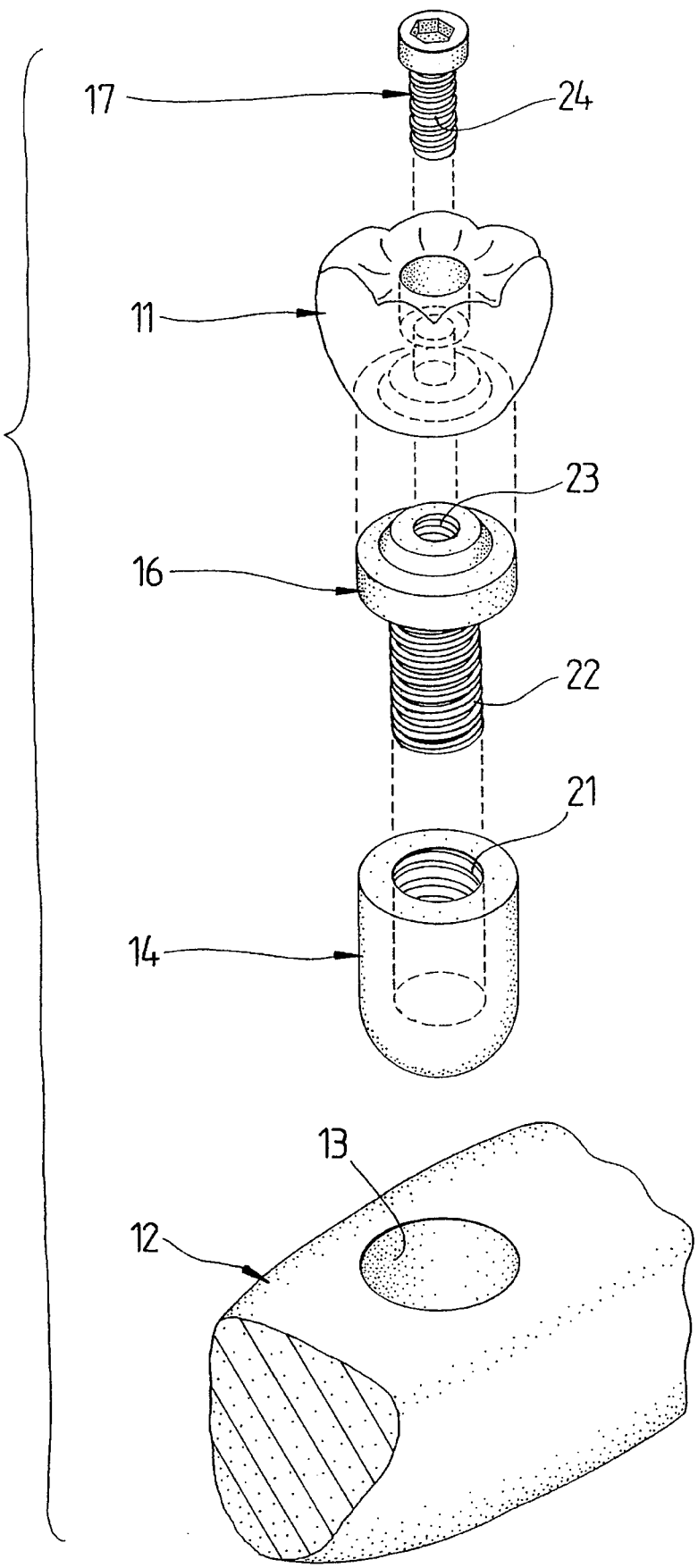
FIG. 1 is an exploded perspective view, partially in section, showing the component parts of a dental implant.

Referring to the drawings for a clearer understanding of the invention, it may be seen in FIG. 1 that the invention is adapted for use in the field of dental implants, wherein a prosthesis, such as a tooth 11 or bridge (not shown), is to be attached to the underlying bone 12. As will be appreciated from the prior art, the surgeon prepares a socket 13 in the bone 12 and positions the implant fixture 14 within the bone 12. The present invention is not directed to the attachment of the fixture 14 to the bone 12; therefore, the external configuration, as shown, is not intended to depict any particular implant fixture. However, the invention is directed to the interaction of the implant 14 with an abutment 16 received therein, and the interaction of the abutment 16 with a screw 17 used to attach the prosthesis 11 to the abutment 16.

Figure 2:
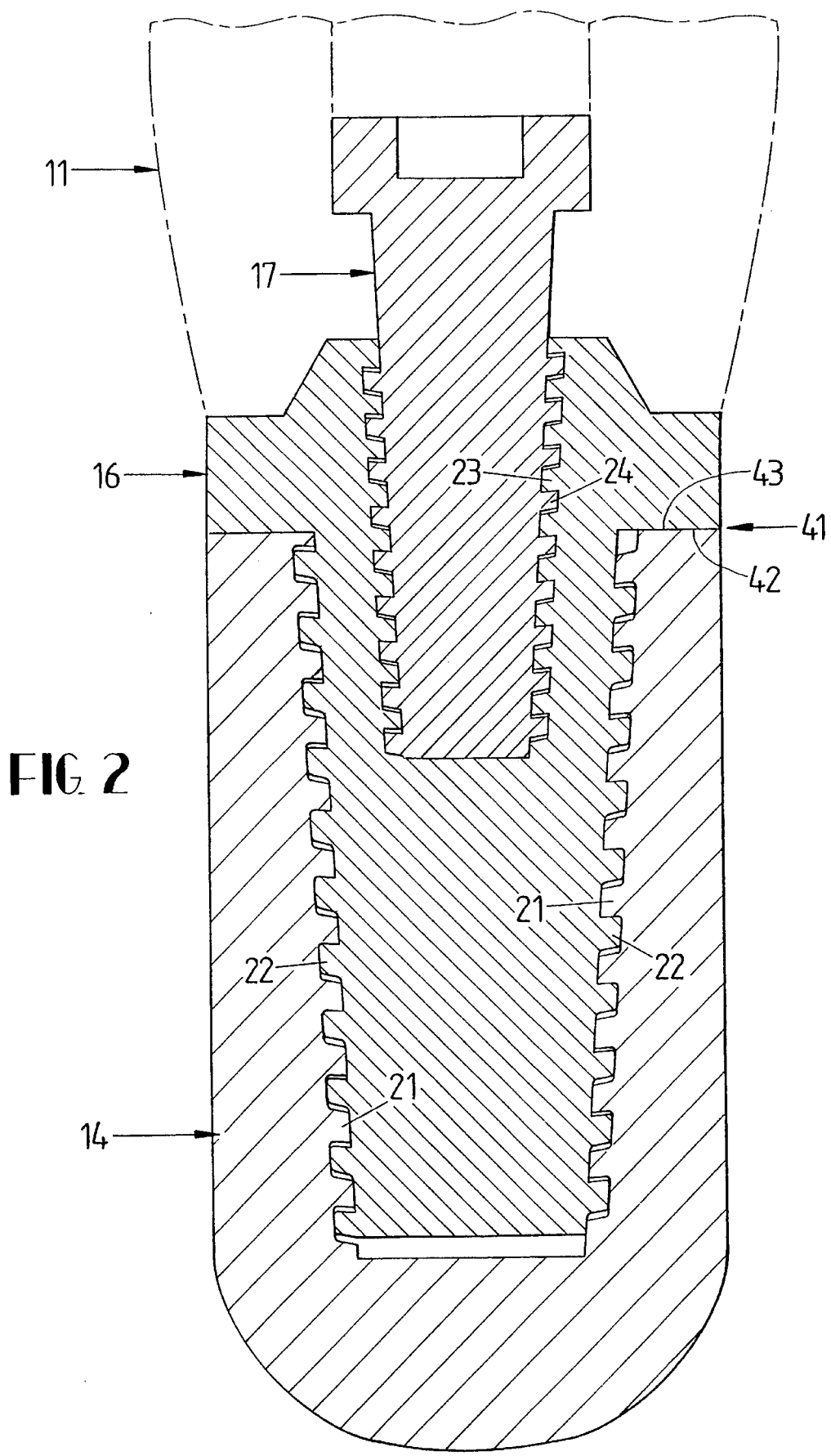
FIG. 2 is a sectional view of the implant assembly along the longitudinal axis.
Figure 3:
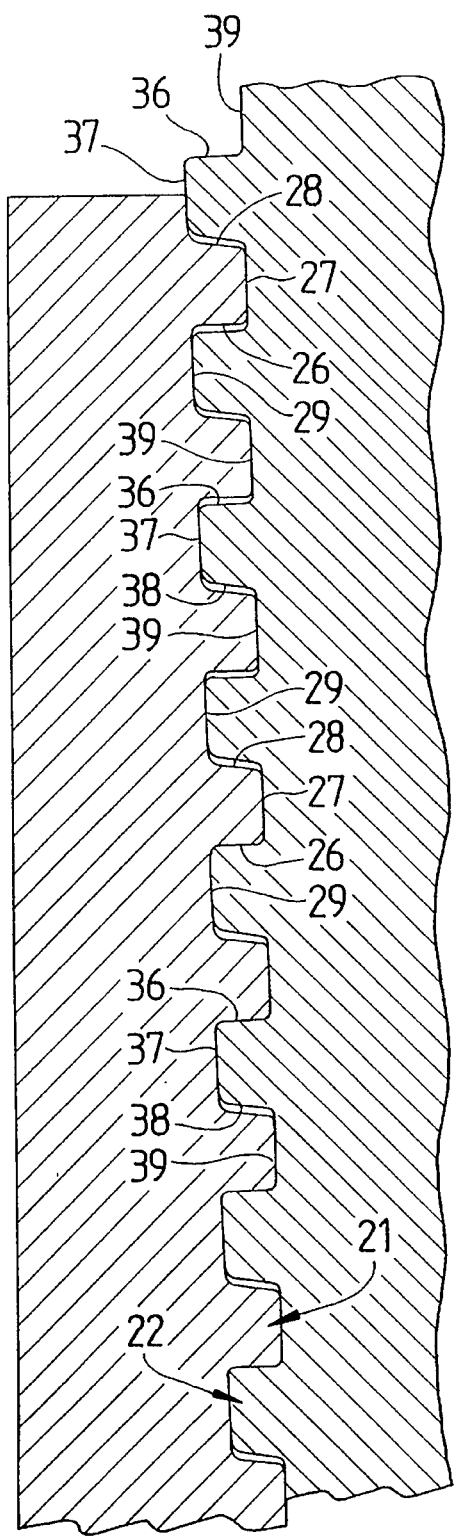
FIG. 3 is a sectional view showing the thread profile of the connection wherein the female thread has a varying lead.
Figure 4:
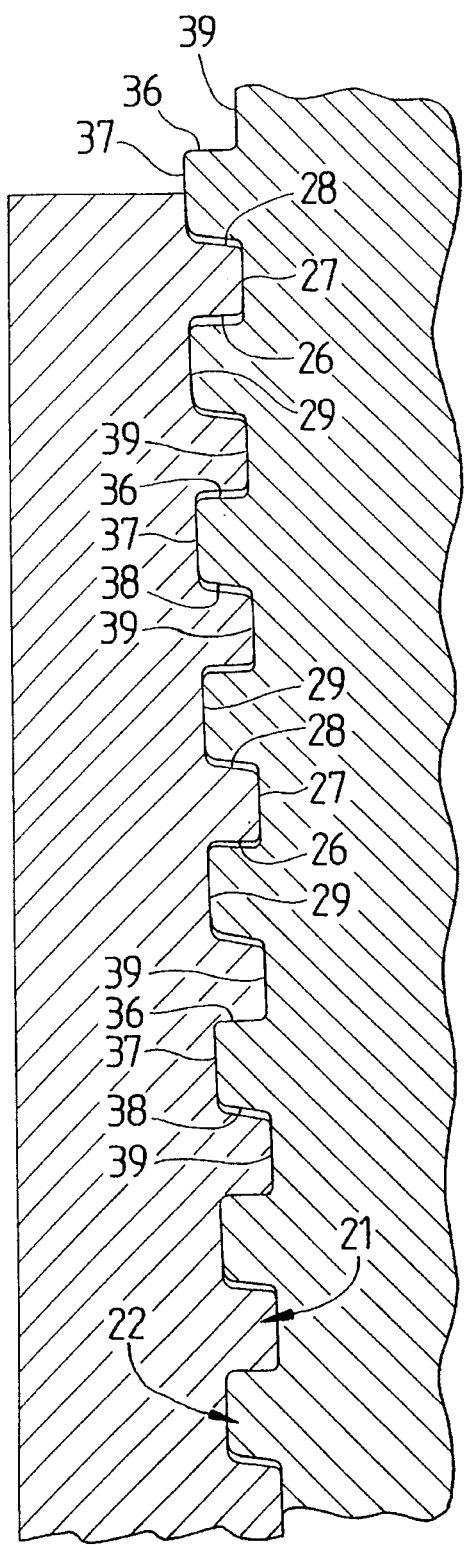
FIG. 4 is a sectional view showing the thread profile of the connector wherein the male thread has a varying lead.

As may be seen more clearly in FIGS. 2–4, the present invention is directed specifically to the formation and the interaction of the threaded connection between the components. Implant 14 has a female thread 21 which cooperatively engages the male thread 22 of the abutment 16. Likewise, abutment 16 has a threaded axial bore wherein female threads 23 are positioned to engage the male thread 24 of screw 17. It will be noted that the profile of the thread is a modified truncated thread, wherein the female thread profile includes a load flank 26 intersecting a crest 27, a stab flank 28 extending from the crest 27 to a root 29, such that the turns of the thread, hereinafter referred to as the threads, along the length of the fastener sequentially repeat the profile, with the crest defining the inner diameter of the thread and the root the outer diameter. Likewise, the male thread profile includes a load flank 36 intersecting a crest 37, and a stab flank 38 extending from the crest 37 to a root 39, such that the threads along the length of the fastener sequentially repeat the profile, with the crest defining the outer diameter of the thread and the root the inner diameter. The thrust connection 41 is usually the abutting portion of the connector which prevents further longitudinal relative movement of the connector components. For example, the abutment 16 may have a shoulder 42 which is urged into contact with the implant surface 43. It will be appreciated that tightening the connector loads the connection by placing the screw, or bolt, under tension between the thrust connection and the load flank interface. If the male thread profile and female thread profile are not properly matched, the connection will not remain secure. Further, dynamic loading, such as by chewing in a dental implant or movement in an orthopedic implant, will also load the connector.

To distribute the stress beyond the end threads, we have altered the lead such that selected load flanks of the threads come into an interfering relationship more rapidly than do other threads. That is to say, the load flank interface of the intermediate threads is effectively moved toward the thrust connection. The lead is altered on either the male or female threads such that a slight variation in lead is created along the length of the connector. The variation of the load flank may be accomplished by varying the thread thickness or axial separation; however, the variation should not diminish the axial clearance of the stab flanks.

By way of example, in FIG. 3, the lead of the male thread is varied while the mating female thread lead remains constant. By varying the lead, the load flanks 26 of the first threads and last threads are slightly separated; whereas the load flanks of the intermediate thread are in forced abutment to generate the pre-load tension in the connection. Therefore, subsequent dynamic loading, which generally affects the end threads to the greatest degree, is now operative on threads which can tolerate the additional load without failure since the pre-load stress is borne by other threads.

Figure 5:
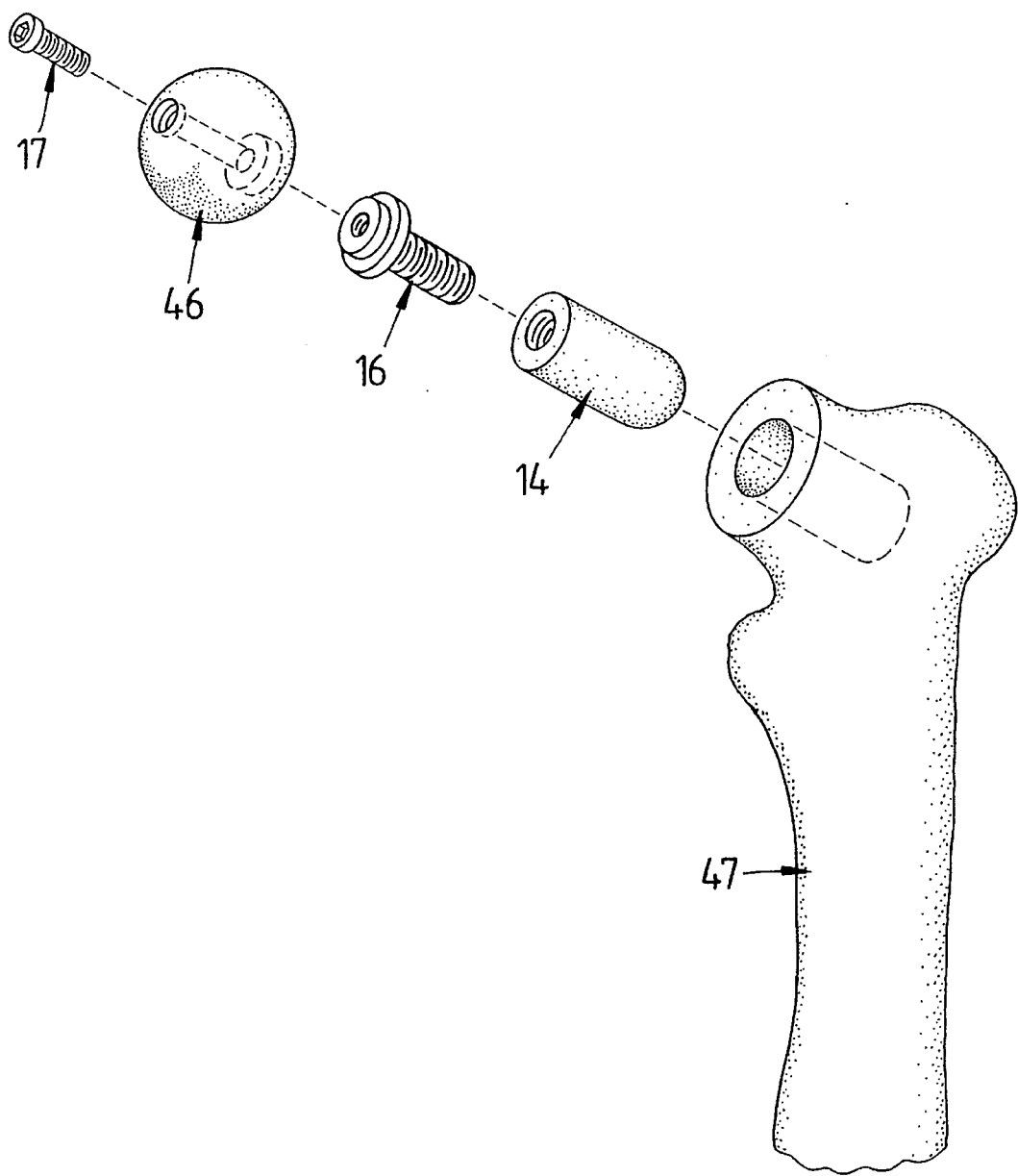
FIG. 5 is an exploded perspective view of the connector used in a hip or other orthopedic implant.

It is further contemplated that the present invention may be used in implants other than dental implants; specifically orthopedic implants. One possibility for the use of the present invention is to permit the interimplant connection of members such that certain parts of the implant could be made modular for standardization rather than unitary. For example, if a socket were to be aligned in a specific plane of the hip, or a ball placed within a socket at a joint, an implant stem affixed to ball, or socket, using the present invention would enable the surgeon to mate the ball and socket and select a stem of appropriate size and length for a particular patient from a set of standard stems and modular and ball or socket units. The present invention would achieve a connection as secure as if the ball or socket were formed with an integral stem. As seen in FIG. 5, a ball 46 is affixed to a bone 47 by means of implant 14, abutment 16 and screw 17.

To accomplish the secure engagement of the connector, the lead is varied in accordance with the formula:

$$L=k+n(x)$$

Where L is the incremental lead or lead between selected turns, k is a constant such as the lead of a reference or nominal turn, n is the incremental deviation from the nominal lead, and x is the number of increments or turns over which the deviation applies. For example, if the lead of the intermediate turn in the above example is used as the constant k, then the separation between the load face on this turn and the load faces on either side thereof increase by n, the incremental deviation times x, where x is 1 and −1 respectively, representing 1 turn from the nominal lead in either direction. Accordingly, the load face whose lead is representative of k would have the least preload clearance when the connector is made up, and the load faces on either side thereof would have an incremental increase in preload clearance, such that the preload stress is borne by the intermediate threads.

In FIGS. 6a and 6b, a connector using my design is shown along with shading to indicate the results of our finite element analysis of the stress levels in the connector. In this example, k is the lead of the engaged thread most remote from the shoulder and the lead in each turn toward the thrust connector decreases by n over the preceding lead. As may be seen, the concentration of stress at the thread closest to the shoulder is significantly reduced.

It should also be noted that the teachings of the present invention may be applied to those implants which are already in existence. For example, in an existing implant-based prosthesis wherein the connector is no longer secure, the present invention may be utilized by providing a new abutment with a variable lead male thread to replace the loosened, or removed abutment. The new abutment may have a variable lead female thread to receive a constant lead attachment screw, or it may have a constant lead female screw to receive a variable lead attachment screw. In either event, if the prosthesis has lost its stability due to the stress between the abutment and the implant, our invention provides a superior replacement abutment. Likewise, if the prosthesis has lost stability due to the stress between the abutment and the attachment screw, then an attachment screw, made in conformity to our invention, provides superior stability.

From the foregoing, it may be seen that we have devised a new and useful thread profile to be used in implant technology which directly addresses the concerns of dynamic and static stress and which can provide a more secure implant structure.

While we have shown our invention in one form, it will be obvious to those skilled in the art that it is not so limited but is susceptible of various changes and modifications without departing from the spirit thereof.

What we claim is:

1. An implant assembly for use in a medical implant, including an implant provided with an abutment for attachment to a prosthesis by a threaded fastener, said abutment and said implant having a cooperative male and female thread and a thrust connection between connected parts, wherein the improvement comprises a thread profile for reducing stress on selected highly stressed threads of said abutment and implant by varying the incremental lead between the male and female thread.

2. An assembly as defined in claim 1, wherein said female thread has a variable lead and said male thread has a constant lead.

3. An assembly as defined in claim 2, wherein said female thread has a profile including a load flank, a stab flank, and interstitial root and crest landings between said load flank and stab flank, and wherein said variable lead moves the load flank of selected turns of the thread away from high axial interference.

4. An assembly as defined in claim 2, wherein the lead of said female thread increases along the length of the fastener.

5. An assembly as defined in claim 1, wherein said male thread has a variable lead and said female thread has a constant lead.

6. An assembly as defined in claim 5, wherein said male thread has a profile including a load flank, a stab flank, and interstitial root and crest landings between said load flank and stab flank, and wherein said variable lead moves the load flank of said male thread away from axial interference with said female thread in selected turns of the thread.

7. An assembly as defined in claim 5, wherein the lead of said male thread varies along the length of the fastener.

8. An assembly as defined in claim 1, wherein said thread profile of each threaded member includes a stab flank positioned such that the stab flanks of each member are held in confronting spaced relation when said threaded members are engaged.

9. An assembly as defined in claim 1, wherein said prosthesis is connected to said abutment by a threaded connector having a male thread for engagement with the female thread of said abutment, said male thread of said prosthesis and said female thread of said abutment having cooperative thread profiles such that pre-load tension stress is distributed along the length of said connector engaged with said abutment.

10. An assembly as defined in claim 9, wherein said female thread has a variable lead and said male thread has a constant lead.

11. An assembly as defined in claim 1, wherein the lead of a selected turn of said thread is varied in accordance with the formula:

$$L = k + n(x)$$

Where, L equals the incremental lead, k equals the lead at a nominal turn, n equals the incremental deviation from the lead of the nominal turn, and x equals the number of increments over which the deviation is applied.

12. An implant assembly for use in a medical implant, including an implant provided with an abutment for attachment to a prosthesis by a threaded fastener, wherein said abutment, said implant, and said fastener each have a cooperative male and female thread and a thrust connection therebetween, wherein the improvement comprises a thread profile for reducing stress on selected threads of said male and female thread by varying the lead of one of the mating threads.

13. An assembly as defined in claim 12, wherein said male and female thread has a profile including a load flank, a stab flank, and interstitial root and crest landings between said load flank and stab flank, and wherein said variable lead, in the selected thread, effectively moves the load flank thereof away from axial interference with the load flank of the other mating thread in selected axial of the connection.

14. An implant assembly in a medical implant, including an implant provided with an abutment for attachment to a prosthesis by a threaded fastener, wherein said abutment, said implant, and said fastener each have a cooperative male and female thread and a thrust connection therebetween, wherein the improvement comprises a thread profile varying the lead of one of the cooperative threads, said male thread of said fastener and said female thread of said abutment having cooperative thread profiles such that the pre-load tension stress is distributed along the length of said fastener engaged with said abutment.

15. An assembly as defined in claim 14, wherein said female thread has a variable lead and said male thread has a constant lead.

16. An assembly as defined in claim 14, wherein said male thread has a variable lead and said female thread has a constant lead.

* * * * *